United States Patent [19]

Ha et al.

[11] Patent Number: 5,505,048
[45] Date of Patent: Apr. 9, 1996

[54] METHOD AND APPARATUS FOR THE SEPARATION OF $C_4$ HYDROCARBONS FROM GASEOUS MIXTURES CONTAINING THE SAME

[76] Inventors: Bao Ha, 807 Wethersfield Dr., Vacaville, Calif. 95688; Gerard Dupuis, 57 Waldale Ct., Walnut Creek, Calif. 94596; Paul Kong, 3303 Richland Dr., Sugar Land, Tex. 77478

[21] Appl. No.: 360,111

[22] Filed: Dec. 20, 1994

Related U.S. Application Data

[62] Division of Ser. No. 64,932, May 5, 1993, Pat. No. 5,414,188.

[51] Int. Cl.⁶ .................................................. F25J 3/02
[52] U.S. Cl. .................................... 62/11; 62/23; 62/39
[58] Field of Search ................................ 62/23, 39, 11

[56] References Cited

U.S. PATENT DOCUMENTS

| | | | |
|---|---|---|---|
| 4,242,875 | 1/1981 | Schaefer | 62/23 |
| 4,336,045 | 6/1982 | Fisher et al. | 62/39 X |
| 4,519,825 | 5/1985 | Bernhard et al. | 62/28 |
| 4,592,766 | 6/1986 | Kumman et al. | 62/39 X |
| 4,664,687 | 5/1987 | Bauer | 62/29 |
| 4,711,651 | 12/1987 | Sharma et al. | 62/23 X |
| 4,746,342 | 5/1988 | DeLong et al. | 62/39 X |
| 4,772,301 | 9/1988 | Bauer | 62/39 X |
| 4,773,968 | 9/1988 | O'Connell et al. | 585/800 |
| 4,832,830 | 5/1989 | Howard | 62/11 |
| 4,921,514 | 5/1990 | Rowles et al. | 62/39 X |
| 5,026,952 | 6/1991 | Bauer | 585/800 |
| 5,329,774 | 7/1994 | Tanguay et al. | 62/23 |

*Primary Examiner*—Christopher Kilner
*Attorney, Agent, or Firm*—Young & Thompson

[57] ABSTRACT

$C_4$ hydrocarbons are separated from a gaseous mixture containing the same and lower hydrocarbons and hydrogen, by cooling such a gaseous mixture (45) to a temperature between $-60°$ F. and $+32°$ F. until a portion of the $C_4$ hydrocarbons is condensed. The mixture of gas and liquid $C_4$ hydrocarbons thus produced is phase separated in a first phase separation (53), and the liquid from this first phase separation is withdrawn as $C_4$ hydrocarbons product (69). Gas from the first phase separation (53) is further cooled (47) until substantially all of the remaining $C_4$ hydrocarbons are condensed but not the hydrogen. The latter material is subjected to a second phase separation (75), and liquid from the second phase separation (77) is withdrawn as liquid $C_4$ hydrocarbons product (69). Vapor from the second phase separation (75) is withdrawn and expanded isentropically in a first expansion engine (81) to produce a mixture of liquid and vapor, which is subjected to a third phase separation (85), and liquid from the third phase separation (85) is withdrawn as liquid $C_4$ hydrocarbons product (69). A portion of vapor separated in the third phase separation (85) is expanded isentropically in a second expansion engine (137), and refrigeration from vapor from the second expansion engine (137) is recovered by indirect heat exchange (47) with the first-mentioned mixture (45). Gas separated in the third separation (85) is cooled to produce a mixture of gas and liquid, which is phase separated (103 or 123). Gas from the latter phase separation is expanded isentropically in the second expansion engine (137), and refrigeration from material from second expansion engine (137) is also recovered by indirect heat exchange (99) with gas separated in the third phase separation (85).

9 Claims, 2 Drawing Sheets

METHOD AND APPARATUS FOR THE SEPARATION OF C₄ HYDROCARBONS FROM GASEOUS MIXTURES CONTAINING THE SAME

This application is a division of application Ser. No. 08/064,932, filed May 5, 1993, now U.S. Pat. No. 5,414,188.

FIELD OF THE INVENTION

The present invention relates to methods and apparatus for the separation of $C_4$ hydrocarbons from gaseous mixtures containing the same.

One such mixture is the product of the dehydrogenation of isobutane to produce isobutene, for example by the catalytic dehydrogenation of isobutane by the "Oleflex" process of UOP Inc., Des Plaines, Ill. 60017. A further disclosure of the Oleflex process is to be found in "Energy Progress", Vol. 6, No.3, September, 1986, pp. 171–176. The isobutene thus produced is separated from the gaseous mixture of unreacted isobutane, hydrogen and lower hydrocarbons, the unreacted isobutane and the hydrogen being returned with makeup isobutane to the dehydrogenation process and the isobutene being used, for example, in the production of methyl tertiary butyl ether, whose use in gasoline in replacement of tetraethyl lead is rapidly increasing.

BACKGROUND OF THE INVENTION

In the past, the separation of $C_4$ hydrocarbons from a gaseous mixture containing hydrogen and perhaps also lighter hydrocarbons has been performed by partial condensation. The feed gas is cooled to a temperature at which the residual hydrocarbon content in the vapor satisfies the requirement of hydrogen purity for the use to which the uncondensed vapor phase is to be put. The liquid phase is then recovered as liquid product. This liquid is normally warmed to ambient temperature to recover its refrigeration.

The Oleflex process produces a gaseous effluent; but this is then cooled and condensed to a liquid fraction containing substantially all the $C_4$ hydrocarbons, which are then separated from each other, the isobutene being a product stream and the liquid isobutane being recycled. The liquid fraction will be about 40–50% of the effluent; and this requires an important supply of refrigeration. As in most cryogenic processes, this refrigeration can be supplied either by a liquid refrigerant, mechanical refrigeration or expansion engines, or a combination of these.

In the past, the liquid isobutane feed stock has been cooled to about –80° F. and has been vaporized by mixing it with hydrogen recycled at lower pressure to produce refrigeration. The feed gas is partially condensed by the refrigeration from the vaporization of the liquid feed stock. The feed gas is further cooled by the use of expansion engines to provide further product recovery. Ordinarily, two expansion engines are used in series, to maximize the efficiency of the equipment, since the final expanded gases are quite light and have an average molecular weight of about 3 to 4.

Such a prior art method and apparatus is shown in FIG. 1 of the accompanying drawings. In FIG. 1, the feed gas, which is the effluent from an Oleflex reactor (not shown), enters the warm end of exchanger 1 via conduit 3 and is cooled and partially condensed and phase separated in separator 5. The liquid from separator 5 is expanded isenthalpically through valve 7 and further separated in separator 9, the liquid from separator 9 being increased in pressure via pump 11 sufficiently that when returned via conduit 13 through exchanger 1, the product leaves exchanger 1 in liquid phase at 15 and then the isobutene is converted to methyl tertiary butyl ether in a conventional unit (not shown), whereafter the latter is separated by conventional fractionation from the isobutane, the liquid isobutane being recycled to the liquid feed 17.

From separator 5, the vapor is expanded isentropically in expansion engine 19 and fed to a phase separator 21. The liquid separated in 21 is expanded isenthalpically through valve 23 to the same pressure as the liquid expanded in valve 7 and joins the latter in passing to separator 9.

The vapor separated in 21 is divided, a portion being removed through conduit 25 as hydrogen product after being used to cool exchanger 1, and the remainder being further expanded isentropically in an expansion engine 27, whose output is phase separated at 29. The liquid from separator 29 is expanded isenthalpically through valve 31 to the same pressure as prevails downstream of valves 7 and 23 and is similarly sent to separator 9.

The vapor from separator 29 is removed through conduit 33 and directed through exchanger 1 to cool the exchanger, whence a portion can be removed, if desired, as hydrogen product at 35; but in any event a large portion of hydrogen from conduit 33 will be merged with liquid feed 17, which has been expanded in valve 37 isenthalpically to the same pressure as in conduit 33, and the mixed liquid and vapor thus produced is completely vaporized in passage toward the warm end of exchanger 1 and leaves exchanger 1 via conduit 39 as the gaseous feed to the Oleflex reactor.

Of course the liquid isobutane in conduit 15 is not sufficient to constitute the liquid feed 17; and so a separate source of liquid isobutane (not shown) provides the required makeup liquid isobutane.

But the process described above has several drawbacks, as follows:

1. The pressure of the feed gas entering via conduit 3 must be high, in order to produce sufficient refrigeration in the expansion engines 19 and 27. Such a high feed gas pressure is not desirable, because the compression equipment is expensive and power consumption is high.
2. An equally unsatisfactory alternative to high feed gas pressure, is the use of mechanical refrigeration at a low temperature level of about –80° F. This can be provided e.g. by an ethylene refrigeration unit in cascade with a propane unit. But such refrigeration equipment is, like the compression equipment, very expensive and its power consumption is high.
3. The purity of the hydrogen in conduit 33, which will be recycled with the liquid feed via conduit 39 to the Oleflex reactor, is low. This results in lower unit capacity and higher operating cost, due to the undesirable presence of lighter hydrocarbons such as methane in this stream.

OBJECTS OF THE INVENTION

It is accordingly an object of the present invention, to provide a method and apparatus for the separation of $C_4$ hydrocarbons from gaseous mixtures containing the same, which is adapted to operate with low-pressure feed gas, thereby saving the initial cost of equipment and the continuing cost of power consumption.

Another object of the present invention is the provision of such a method and apparatus, which minimizes or even eliminates the use of mechanical refrigeration, thereby again to save initial equipment cost and continuing power cost.

A still further object of the present invention is to provide such a method and apparatus, in which higher purity hydrogen will be produced for recycle to an isobutane dehydrogenation unit or for other purposes.

SUMMARY OF THE INVENTION

The above and other objects and advantages of the present invention are achieved, by providing a method and apparatus for the separation of $C_4$ hydrocarbons from a gaseous mixture containing the same, wherein the feed is initially cooled to only a relatively high temperature level, between about −60° F. to +32° F., preferably -30° F to 10° F, at which temperature level only a portion thereof is liquefied. This mixture is phase separated, and the separated liquid is handled as in the known process. The separated vapor, however, is subjected to further cooling and partial condensation until substantially all the $C_4$ hydrocarbon are condensed, and is then phase separated and the separated phase is subjected to isentropic expansion in a series of two expansion engines. According to another important feature of the present invention, refrigeration by indirect heat exchange is provided, between the two expansion engines, with phase separation and isentropic expansion of only the remaining gas phase in the second expansion engine.

As a result, the energy required to perform the necessary condensations is much smaller than previously, which results in a saving of compression or a saving of refrigeration or both. Moreover, the purity of the hydrogen subjected to the second isentropic expansion is substantially higher than in the past.

BRIEF DESCRIPTION OF THE DRAWINGS

The above and other objects, features and advantages of the present invention will become more apparent from a consideration of the following description, taken in connection with the accompanying drawings, in which.

DETAILED DESCRIPTION OF THE PREFERRED EMBODIMENT

Figure 2:
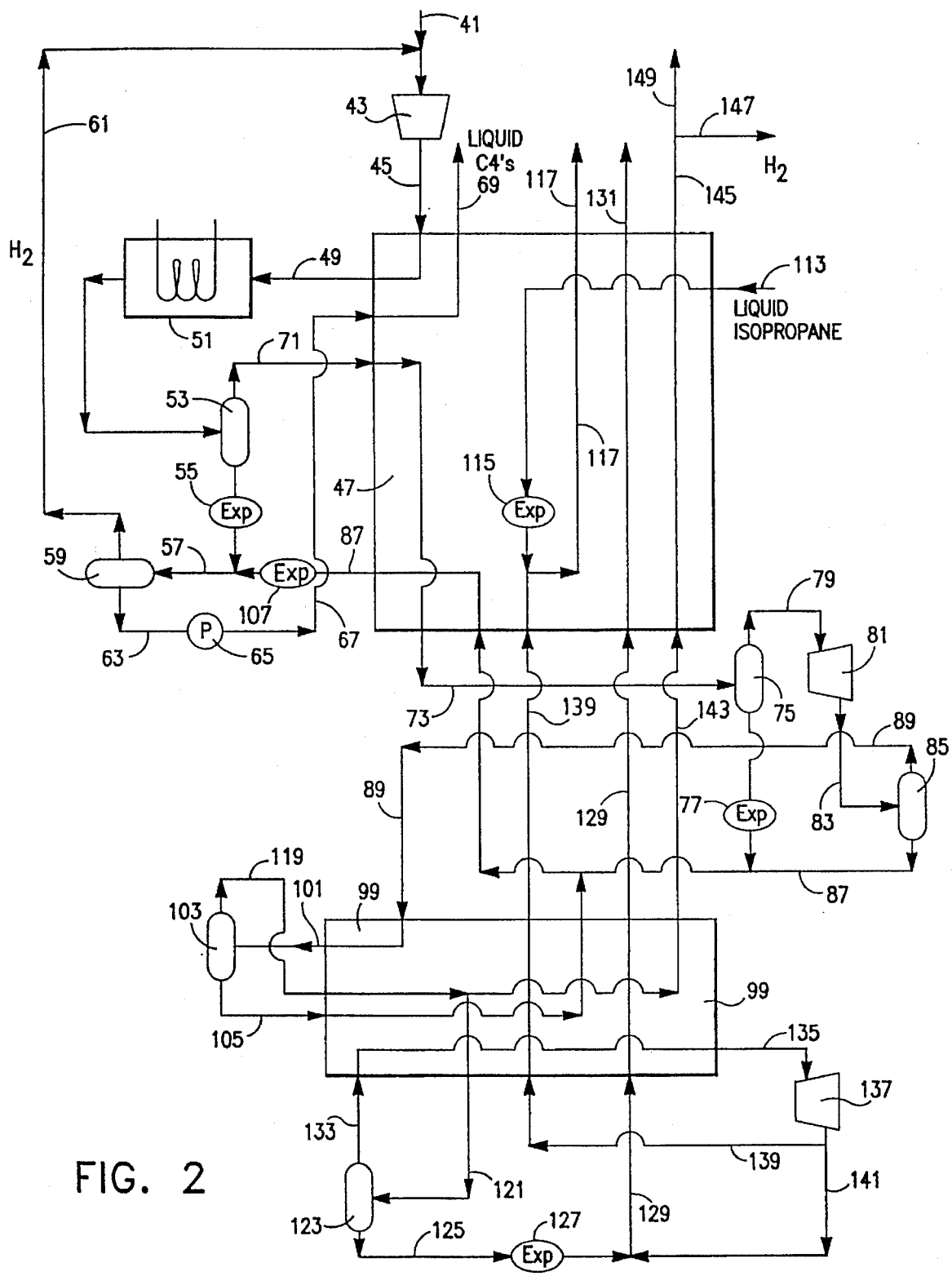
FIG. 2 is a diagrammatic view of a separation cycle according to the present invention.

Referring now to the drawings in greater detail, and specifically to FIG. 2 thereof, there is shown a method and apparatus according to the present invention, for the separation of isobutene and isobutane from a mixture containing not only these two $C_4$ hydrocarbons, but also lower hydrocarbons and a substantial proportion of hydrogen.

The principal feed to the cycle shown in FIG. 2 is via conduit 41, through which is supplied gaseous effluent from an Oleflex reactor, at about atmospheric pressure and a temperature of 115° F. The feed gas is compressed in a compressor 43 to a pressure of 90 psia and a temperature of 115° F., and enters the system of the present invention via a conduit 45. Upon entry, the mixture has the following mole percent composition:

| | |
|---|---|
| $H_2$ | 50 |
| $CH_4$ | 7 |
| $C_3H_8$ | 2 |
| $C_4H_{10}$ | 17 |
| $C_4H_8$ | 18 |
| Balance: $C_2H_4$, $C_2H_6$, $C_3H_6$, $C_4H_6$, $C_5H_{10}$ | |

This gaseous mixture is fed to a main heat exchanger 47 for cooling therein. But instead of passing entirely through exchanger 47 this stream is withdrawn from exchanger 47 through a conduit 49, when the feed has been cooled to a temperature in the broad range of 60° F. to +32° F., more particularly −30° F. to 10° F., and in this illustrated embodiment, −25° F. If desired, this latter temperature can be reached by providing external refrigeration in a cooler 51, using a conventional refrigerant at the appropriate temperature level; but cooler 51 must be understood to be optional: one of the advantages of the present invention is that little or no such external refrigeration is needed, with consequent savings of equipment and power consumption. And even if such mechanical refrigeration is provided, it is provided at a relatively high temperature and so is much less expensive than in the prior art.

The feed, at the mentioned temperature of −25° F., is then sent to a phase separator 53, the liquid phase produced therein being isenthalpically expanded through a Joule-Thomson expansion valve 55 to about atmospheric pressure. The resulting gas-liquid mixture then passes through conduit 57 to a flash drum 59, whence the vapor, having a hydrogen content of about 30%, is withdrawn through conduit 61 and recycled to the feed in conduit 41.

The liquid from flash drum 59 is withdrawn through conduit 63 and pumped in pump 65 to a pressure of 300 psig, and is then returned via conduit 67 through the warm end of exchanger 47 to help cool the same. The pressure imparted by pump 65 is sufficient to prevent vaporization of the liquid upon warming in exchanger 47, and so a net liquid product is withdrawn from exchanger 47 via conduit 69 and sent to a conventional treatment (not shown) wherein the isobutene is converted to methyl tertiary butyl ether, which is separated from the isobutane by conventional fractionation, the latter being recycled to the isobutane makeup stream to be described later. In any event, the separation and subsequent utilization of the individual $C_4$ hydrocarbons forms no part of the present invention, which is concerned solely with the separation of $C_4$ hydrocarbons from lower hydrocarbons and hydrogen in gaseous mixtures containing the same.

The vapor from separator 53 is withdrawn through conduit 71 and reintroduced into exchanger 47 at its appropriate temperature level, whence it proceeds through exchanger 47 to the cold end thereof, exiting through conduit 73 at a temperature of −120° F. The partially condensed stream in conduit 73, in which substantially all the remaining $C_4$ hydrocarbons are in liquid phase, is then supplied to a phase separator 75, from which the liquid is expanded isenthalpically through valve 77 to about atmospheric pressure and returned to the cold end of exchanger 47 as will be described hereinafter.

The vapor is withdrawn overhead from separator 75 through conduit 79 at the aforesaid temperature of −120° F. and pressure of 90 psia and subjected to isentropic expansion in a first expansion engine 81, which it leaves in mixed vapor-liquid phase at a temperature of −130° F. and a pressure of 70 psia, via conduit 83, and is fed to a phase separator 85. From separator 85, the liquid is withdrawn through conduit 87 and joins the material from expansion valve 77.

The vapor overhead is withdrawn from separator 85 through conduit 89 and contains about 88% hydrogen. It is introduced into the warm end of a further heat exchanger 99, which it enters at the above-mentioned temperature of −130° F. It is cooled in exchanger 99 to −190° F. and withdrawn via conduit 101 and proceeds to phase separator 103. The liquid from separator 103 reenters exchanger 99 via conduit 105 and is warmed and partially vaporized therein and combined with the material in conduit 87, this combined stream being warmed somewhat in the cold end of exchanger 47 and expanded to about atmospheric pressure in a Joule-Thomson expansion valve 107, whence it joins the material from expansion valve 55 for phase separation in flash drum 59, as explained above. This treatment of the liquid from separator 103 improves the $C_4$ recovery and minimizes the risk of freezing of heavy hydrocarbons at the cold end of exchanger 99.

The isobutane feed, in liquid phase at a pressure of 110 psia and a temperature of 110° F., is supplied via conduit 113 to an appropriate temperature level in exchanger 47, in which it is cooled and then expanded in Joule-Thomson expansion valve 115 to a pressure of 50 psia, and combined with the stream in conduit 139, the mixed streams giving up their refrigeration to the feed in exchanger 47 and emerging from exchanger 47 via conduit 117 in vapor phase at a temperature of 115° F. This vapor constitutes the feed to the mentioned Oleflex reactor.

The gaseous overhead from phase separator 103 is withdrawn through conduit 119 and introduced at its appropriate temperature level into exchanger 99, in which a portion of it is cooled to −270° F. and partially condensed. This portion is withdrawn from exchanger 99 via conduit 121 and fed to phase separator 123. The liquid from separator 123, which is mostly methane, is withdrawn via conduit 125 and is expanded through Joule-Thomson expansion valve 127 and is withdrawn via conduit 129, in which it is warmed successively in exchangers 99 and 47 and leaves the cycle via conduit 131 as fuel gas.

The remainder of the overhead from phase separator 103 flows through conduit 143 wherein it is warmed and then is further warmed in exchanger 47 which it leaves through conduit 145. A portion can be withdrawn through conduit 147 as an impure hydrogen product and the remainder can be withdrawn through conduit 149 as catalyst regeneration lift gas. This treatment of the remainder of the overhead from separator 103 results in an improvement of hydrogen purity as compared to the overhead from separator 85.

The overhead from separator 123, which is mostly hydrogen, is withdrawn through conduit 133, warmed in exchanger 99 to −265° F., withdrawn from exchanger 99 at that temperature and at a pressure of 70 psia via conduit 135 and is expanded isentropically in second expansion engine 137 to 50 psia and a temperature of −280° F. A portion of the material from expansion engine 137 is withdrawn through conduit 139, whence it joins the vapor feed to the reactor. The balance of the output from engine 137 is fed via conduit 141 to conduit 129 in which it joins the fuel gas leaving the cycle.

Figure 1:
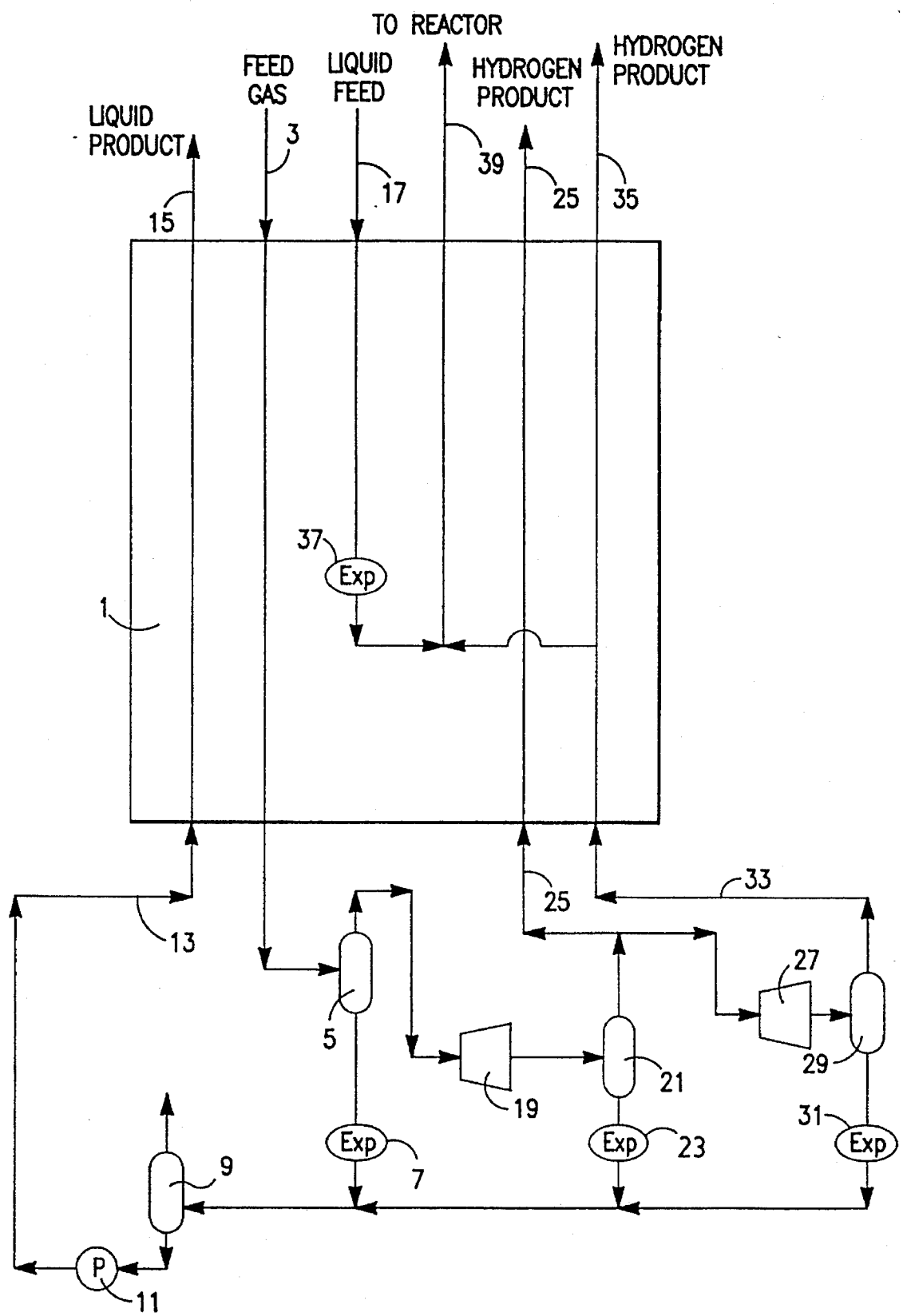
FIG. 1, as previously indicated, is a diagrammatic view of a separation cycle according to the prior art.

Now comparing the prior art of FIG. 1 with the present invention of FIG. 2, it will be noted that certain components have identifiable counterparts, among them being those identified by reference numeral in the following table:

| Component | FIG. 1 | FIG. 2 |
|---|---|---|
| Feed conduit | 3 | 45 |
| Heat exchanger | 1 | 47 |
| Phase separator | 5 | 75 |
| First expansion engine | 19 | 81 |
| Subsequent phase separator | 21 | 85 |
| Second expansion engine | 27 | 137 |

Bearing in mind those points of similarity, it will be seen that the present invention provides, inter alia, relative to the prior art as represented by FIG. 1, the following two principal points of novelty:

1. In FIG. 1, the same feed proceeds via conduit 3 entirely through exchanger 1. By contrast, in the present invention, the feed is cooled to only a relatively high temperature level in conduit 45, and phase separated in separator 53, the resulting liquid being either recycled or withdrawn from the cycle, or both. Only the overhead from separator 53 is further processed as feed according to the present invention, with great saving in compression and/or saving in mechanical refrigeration.

2. In the prior art as represented by FIG. 1, the vapor produced in the first expansion engine 19 is supplied as such as to the second expansion engine 27. Hence, the vapor separated in separator 29 downstream from the second expansion engine 27 will contain an undesirably high proportion of methane, which will be fed to the reactor via conduit 39. By contrast, in the present invention, at least a portion of the vapor formed in first expansion engine 81 will be further cooled by indirect heat exchange in exchanger 99, and then phase separated, only the overhead form this latter phase separation supplying the second expansion engine 137. This increases the purity of hydrogen available for recycle purposes: the methane is condensed by this lower temperature indirect heat exchange and can be removed from the cycle, e.g. in the fuel gas leaving conduit 131, and is not returned to the reactor.

Secondary features of novelty of the present invention include the following:

3. The first feature of novelty recited above need not be bought at the cost of decreased production of $C_4$ hydrocarbons: downstream of separator 53, a further separation is effected by expansion at 55, the resulting liquid joining that separated in separators 75 and 85 to constitute the net liquid product of $C_4$ hydrocarbons.

4. At the same time, the vapor from flash drum 59 can be recycled via conduit 61 to the feed.

5. The cooling by indirect heat exchange at a lower temperature level, in exchanger 99, can be further refined by further cooling the overhead separated in separator 103, in exchanger 99, for still further phase separation at 123, by which a liquid stream which is mostly methane can be removed via conduit 125 and sent to an innocuous use such as fuel gas via conduit 131.

6. Also as a result of the further phase separation in 123, the effluent from second expansion engine 137 is sufficiently pure to join the reactor feed supplied via conduits 139 and 113 and exiting via conduit 117.

7. Because the liquid from separator 103 is warmed in conduit 105, the risk of freezing of heavy hydrocarbons is minimized; and the subsequent treatment of this material improves the $C_4$ recovery.

8. The use of the overhead from separator 103 as hydrogen product improves hydrogen purity as compared to the overhead from separator 85.

From a consideration of the foregoing disclosure, therefore, it will be seen that all of the initially recited objects of the present invention have been achieved.

Although the present invention has been described and illustrated in connection with a preferred embodiment, it is to be understood that modifications and variations may be resorted to without departing from the spirit of the invention, as those skilled in this art will readily understand. For example, although we have diagrammatically indicated the expansion engines to be expansion turbines, other types of expansion engine could be used. Also, although we have shown two heat exchange units, it is to be understood that each of these could be subdivided as required. Finally, although we have recited particular pressures, temperatures and compositions, these can vary as required and are given only for illustrative purposes. These and other modifications and variations will be apparent to persons of ordinary skill in this art and so are to be construed as being comprehended by the scope of the present invention as defined by the appended claims.

What is claimed is:

1. Apparatus for separating $C_4$ hydrocarbons from a gaseous mixture containing the same and lower hydrocarbons and hydrogen, comprising means for cooling said gaseous mixture (45) to a temperature between −60° F. and +32° F. until a portion of said $C_4$ hydrocarbons is condensed, means for phase separating a mixture of gas and liquid $C_4$ hydrocarbons thus produced in a first phase separation (53), means for withdrawing liquid from said first phase separation as $C_4$ hydrocarbons product (69), means for withdrawing gas from said first phase separation (53) and further cooling the same (47) until substantially all of the remaining $C_4$ hydrocarbons are condensed but not the hydrogen, means for subjecting the further cooled material to a second phase separation (75), means for withdrawing liquid from said second phase separation (77) as liquid $C_4$ hydrocarbons product (69), means for withdrawing vapor from said second phase separation (75) and expanding the same isentropically in a first expansion engine (81) to produce a mixture of liquid and vapor, means for subjecting the latter mixture to a third phase separation (85), means for withdrawing liquid from said third phase separation (85) as liquid $C_4$ hydrocarbons product (69), means for expanding a portion of vapor separated in said third phase separation (85) isentropically in a second expansion engine (137), and means for recovering refrigeration from vapor from said second expansion engine (137) by indirect heat exchange (47) with the first-mentioned mixture (45).

2. Apparatus as claimed in claim 1, and means for expanding isenthalpically (55) liquid from said first phase separation (53) to produce a mixture of vapor and liquid, means for separating (59) the latter mixture into vapor and liquid, means for pumping (65) the latter liquid to elevated pressure, and means for recovering refrigeration from the pumped liquid by indirect heat exchange (47) with the first-mentioned mixture (45).

3. Apparatus as claimed in claim 2, and means for recycling (61) vapor from the last-mentioned separation (59) to the first-mentioned mixture (45).

4. Apparatus as claimed in claim 1, and means for expanding isenthalpically liquid from said first separation (53) to produce a liquid-vapor mixture, phase separating (59) the latter mixture, and means for recycling vapor from the last-named phase separation to the first-mentioned mixture (45).

5. Apparatus for separating $C_4$ hydrocarbons from a gaseous mixture containing the same and lower hydrocarbons and hydrogen, comprising means for cooling said gaseous mixture until substantially all of the $C_4$ hydrocarbons are condensed but not the hydrogen, means for subjecting the cooled mixture to a first phase separation (75), means for withdrawing liquid from said first phase separation (77) as liquid $C_4$ hydrocarbons product (69), means for withdrawing vapor from said first phase separation (75) and expanding the same isentropically in a first expansion engine to produce a mixture of liquid and vapor, means for subjecting the latter mixture to a second phase separation (85), means for withdrawing liquid from said second phase separation (85) as liquid $C_4$ hydrocarbons product (69), means for cooling gas (99) separated in said second separation (85) to produce a mixture of gas and liquid, means for subjecting the latter mixture to phase separation (103 or 123), means for expanding gas from the latter phase separation isentropically in a second expansion engine (137), and means for recovering refrigeration from material from said second expansion engine (137) by indirect heat exchange (99 and 47) with gas separated in said second phase separation (85) and with the first-mentioned mixture (45).

6. Apparatus as claimed in claim 5, and means for conducting said cooling (99) of gas separated in said second phase separation (85) in first and second stages with phase separation (103 and 123) following each said cooling stage, and means for supplying to said second expansion engine (137) only gas (133) from said second cooling stage.

7. Apparatus as claimed in claim 6, and means for recovering refrigeration from liquid separated by phase separation (103 and 123) following both of said first and second cooling stages, by said indirect heat exchange (99 and 47).

8. Apparatus as claimed in claim 6, and means for withdrawing liquid from said first stage phase separation (103) as $C_4$ hydrocarbons product.

9. Apparatus as claimed in claim 6, and means for withdrawing as hydrogen product a portion of gas separated in said first stage phase separation (103).

* * * * *